United States Patent [19]

Suhadolnik et al.

[11] Patent Number: 5,410,047
[45] Date of Patent: Apr. 25, 1995

[54] POLYMER STABILIZERS CONTAINING BOTH HINDERED AMINE AND HYDROXLAMINE MOIETIES

[75] Inventors: Joseph Suhadolnik, Ossining; Ramanathan Ravichandran, Nanuet, both of N.Y.; Valerio Borzatta; Graziano Vignali, both of Bologna, Italy

[73] Assignee: Ciba-Geigy Corporation, Ardsley, N.Y.

[21] Appl. No.: 3,068

[22] Filed: Jan. 11, 1993

Related U.S. Application Data

[62] Division of Ser. No. 606,403, Oct. 31, 1990, Pat. No. 5,202,441.

[30] Foreign Application Priority Data

Nov. 7, 1989 [IT] Italy .................... 22293/89

[51] Int. Cl.$^6$ ................... C07D 401/02; C07D 401/14
[52] U.S. Cl. ................... 544/198; 544/113; 544/207; 544/212
[58] Field of Search ................... 524/100; 544/198, 113, 544/207, 212

[56] References Cited

U.S. PATENT DOCUMENTS

| 3,925,376 | 12/1975 | Chalmers et al. | 524/100 |
|---|---|---|---|
| 4,533,688 | 8/1985 | Toda et al. | 524/100 |
| 4,590,231 | 5/1986 | Seltzer et al. | 524/100 |
| 4,665,185 | 5/1987 | Winter et al. | 546/184 |
| 4,668,721 | 5/1987 | Seltzer et al. | 524/95 |
| 4,668,722 | 5/1987 | Mack | 524/103 |
| 4,670,488 | 6/1987 | Maegawa et al. | 524/103 |
| 4,691,015 | 9/1987 | Behrens et al. | 524/102 |
| 4,691,101 | 9/1987 | Behrens et al. | 544/198 |
| 4,782,105 | 1/1988 | Rairchandran et al. | 524/236 |
| 4,876,300 | 10/1989 | Seltzer et al. | 524/100 |
| 4,921,893 | 5/1990 | Avar | 524/99 |
| 4,972,009 | 11/1990 | Suhadolnik et al. | 524/99 |
| 4,976,889 | 12/1990 | Aumueller et al. | 252/403 |
| 5,004,770 | 4/1991 | Cortolano et al. | 524/99 |
| 5,006,577 | 4/1991 | Behrens et al. | 524/95 |
| 5,026,749 | 6/1991 | Cantatore et al. | 524/99 |

FOREIGN PATENT DOCUMENTS 0316582  5/1989  European Pat. Off. .

OTHER PUBLICATIONS

Klemchuck et al., "Stabilization Mechanisms of Hindered Amines" Polymer Degradation & Stability 22 (1988) 241–274.

Primary Examiner—Kriellion S. Morgan
Attorney, Agent, or Firm—Luther A. R. Hall

[57] ABSTRACT

Compounds possessing both a hindered amine moiety, such as a derivative of 2,2,6,6-tetramethylpiperidine, and a hydroxylamine moiety where the N-hydroxy group is not attached to a nitrogen atom in a piperidine ring are valuable stabilizers for protecting polymer compositions against the deleterious effects of actinic light and from the adverse effects of high temperature polymer processing environments.

7 Claims, No Drawings

POLYMER STABILIZERS CONTAINING BOTH HINDERED AMINE AND HYDROXLAMINE MOIETIES

This is a divisional of application Ser. No. 07/606,403, filed on Oct. 31, 1990, now U.S. Pat. No. 5,202,441, issued on Apr. 13, 1993.

The instant invention pertains to compounds, and to compositions stabilized therewith, which possess both a hindered amine moiety and a hydroxylamine moiety in the same moiety and where the N-hydroxy group is not attached to the N-atom of the piperidine ring.

BACKGROUND OF THE INVENTION

The hindered amines, such as the derivatives of 2,2,6,6-tetramethylpiperidine have long been known as very effective stabilizers against the deleterious effects of actinic light. Indeed, a number of such compounds enjoy considerable economic success as light stabilizers for a host of organic substrates.

Hydroxylamines are known as stabilizers for various polymeric systems either when used alone or in conjunction with phenolic antioxidants, organic phosphorus compounds, hindered amines or the like, as is taught in U.S. Pat. Nos. 4,590,231 and 4,782,105, and 4,876,300.

Hindered amines substituted by a hydroxyl group on the N-atom of the piperidine ring are also known and are found to be effective processing stabilizers as taught in U.S. Pat. Nos. 4,590,231; 4,668,721 and 4,691,015. The instant compounds have both a hindered amine moiety and a hydroxylamine moiety where the N-OH group is not part of a piperidine ring. Such compounds are novel and allow for much greater flexibility in molecular structures than do the hydroxylamines of the prior art.

This can be especially seen where the N-atom of the hindered amine is substituted by a hydrocarboxy group. Such groups are non-interacting and allow the hindered amine to be used in poly(vinyl chloride), PVC, and acid catalyzed thermoset acrylic coatings where hindered amines with high basicity sometimes cause problems.

OBJECTIVES OF THE INVENTION

One object of the invention is to provide a compound having both a hindered amine moiety and a hydroxylamine moiety in the same molecule so that one stabilizer can be used to achieve light stability and process stability for various polymer substrates.

Another object of the invention is to provide polymer compositions stabilized by having at least one of the instant compounds present.

DETAILED DISCLOSURE

The instant invention relates to compounds of formula I, II, III or IV

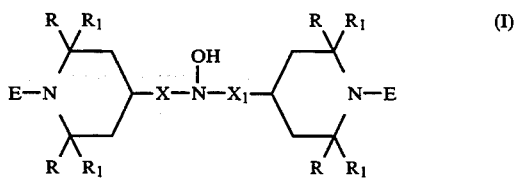

(I)

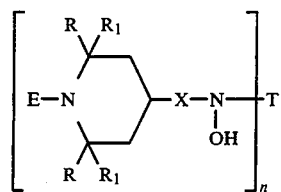

(II)

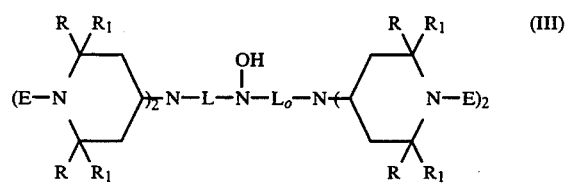

(III)

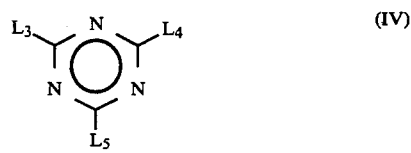

(IV)

wherein

E is hydrogen, oxyl, hydroxyl, alkyl of 1 to 18 carbon atoms, alkenyl of 3 to 18 carbon atoms, aralkyl of 7 to 9 carbon atoms, cycloalkyl of 5 to carbon atoms, hydroxyalkyl of 2 to 6 carbon atoms, alkoxyalkyl of 2 to 20 carbon atoms, alkanoyl of 1 to 18 carbon atoms, alkoxy of 1 to 18 carbon atoms, cycloalkoxy of 5 to 12 carbon atoms, aryloxy of 6 to 10 carbon atoms, hydroxyalkoxy of 2 to 6 carbon atoms, alkoxyalkoxy of 2 to 20 carbon atoms, aralkoxy of 7 to 15 carbon atoms or a bicyclo or tricycloaliphatic oxy radical of 7 to 12 carbon atoms, R and $R_1$ are independently alkyl of 1 to 4 carbon atoms or together R and $R_1$ are pentamethylene, X and $X_1$ are independently a direct bond or Q—G, where Q is —O—, —COO—, —OCO— or —$NR_2$—, $R_2$ is hydrogen, alkyl of 1 to 12 carbon atoms, cycloalkyl of 5 to 12 carbon atoms, cyanoethyl, aryl of 6 to 10 carbon atoms, aralkyl of 7 to 15 carbon atoms, $C_2$–$C_4$-alkyl which is substituted in the 2-, 3- or 4-position bynn $C_1$–$C_8$-alkoxy or by di($C_1$–$C_4$-alkyl)-amino, tetrahydrofurfuryl or —$CH_2CHR_3OH$, and $R_3$ is hydrogen, methyl or phenyl, with Q being attached to the piperidinyl ring, G is alkylene of 1 to 4 carbon atoms, arylene of 6 to 10 carbon atoms or arylene-alkylene of 7 to 15 carbon atoms, n is 1, 2, 3 or 4, when n is 1, T is hydrogen, alkyl of 1 to 36 carbon atoms, said alkyl interrupted by one or more oxygen atoms, cycloalkyl of 5 to 12 carbon atoms, aralkyl of 7 to 9 carbon atoms, or said aralkyl substituted by alkyl of 1 to 4 carbon atoms or by one or two halogen atoms, cyanoethyl, alkenyl of 2 to 8 carbon atoms, alkoxycarbonylalkyl of 4 to 36 carbon atoms where alkyl is of 1 to 4 carbon atoms, or T is

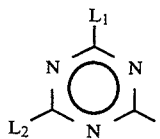

where $L_1$ and $L_2$ are independently $-OR_4$, $-SR_4$ or $-NR_5R_6$ where $R_4$ is alkyl of 1 to 18 carbon atoms, and $R_5$ and $R_6$ are independently hydrogen, alkyl of 1 to 18 carbon atoms, 2,2,6,6-tetramethyl-4-piperidyl, 1,2,2,6,6-pentamethyl-4-piperidyl, tetrahydrofurfuryl, $C_2$-$C_4$-alkyl which is substituted in the 2-, 3- or 4-position by OH, by $C_1$-$C_8$-alkoxy or by di($C_1$-$C_4$-alkyl)amino or

is a 5- to 7- membered heterocyclic group, or $L_1$ is $-NR_5OH$, when n is 2, T is alkylene of 2 to 12 carbon atoms, arylene of 6 to 10 carbon atoms, xylylene, $-CH_2CHOHCH_2-$, $-CH_2CHOHCH_2-O-G_1-O-CH_2CHOHCH_2-$, $-CH_2$-phenylene-COO-$G_1$-OCO-phenylene-$CH_2-$, $-CH_2CH_2-COO-G_1-OCO-CH_2CH_2-$ or $-CH_2$-phenylene-$CH_2-OCO-G_1-COO-CH_2$-phenylene-$CH_2-$, $G_1$ is alkylene of 2 to 12 carbon atoms, arylene of 6 to 10 carbon atoms or cycloalkylene of 6 to 12 carbon atoms, or T is

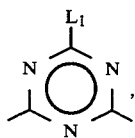

when n is 3, T is alkanetriyl of 3 to 6 carbon atoms, 2,4,6-triazinyl or is

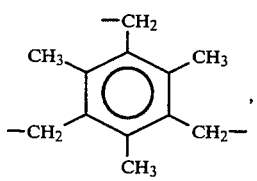

when n is 4, T is alkanetetrayl of 4 to 6 carbon atoms,

L and $L_o$ are independently $-CO$-alkylene of 3 to 6 carbon atoms, or $-CO$-phenylene-$CH_2-$, with the carbonyl group being attached to the N-atom attached to the piperidinyl rings, $L_3$, $L_4$ and $L_5$ independently have the same meaning as $L_1$ or

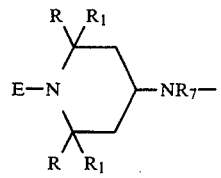

where $R_7$ is hydrogen, hydroxyl, alkyl of 1 to 12 carbon atoms or

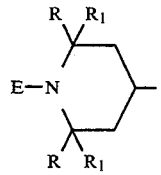

with the proviso that at least one of $L_3$, $L_4$ and $L_5$ is

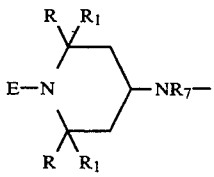

where $R_7$ is hydroxyl, or is $-NR_5OH$.

Preferably E is hydrogen, hydroxyl, alkyl of 1 to 12 carbon atoms, allyl, benzyl, alkanoyl of 2 to 4 carbon atoms, alkoxy of 1 to 12 carbon atoms, cyclohexyloxy or alpha-methylbenzyloxy.

Most preferably E is hydrogen, hydroxyl, alkyl of 1 to 4 carbon atoms, allyl, benzyl, acetyl, methoxy, heptyloxy, octyloxy, nonyloxy or cycloheyloxy.

R and $R_1$ are preferably each methyl.

X and $X_1$ are preferably the same and are a direct bond or are $-OCO$-phenylene-$CH_2-$.

When n is 1, T is preferably hydrogen, alkyl of 1 to 18 carbon atoms, benzyl or alkoxycarbonylalkyl of 4 to 18 carbon atoms where the alkyl is of 2 to 4 carbon atoms.

Most preferably, when n is 1, T is alkyl of 1 to 12 carbon atoms, benzyl or alkoxycarbonylethyl of 4 to 15 carbon atoms.

When n is 2, T is preferably alkylene of 2 to 8 carbon atoms, p-xylylene, $-CH_2$-phenylene-COO-$G_1-OCO$-phenylene-$CH_2-$, $-CH_2CH_2-COO-G_1-OCO-CH_2CH_2-$ or $-CH_2$-phenylene-$CH_2-OCO-G_1-COO-CH_2$-phenylene-$CH_2-$ where $G_1$ is alkylene of 2 to 10 carbon atoms, Most preferably, when n is 2, T is alkylene of 4 to 8 carbon atoms or $-CH_2$-phenylene-COO-$G_1$-OCO-phenylene-$CH_2-$, $-CH_2CH_2-COO-G_1-OCO-CH_2CH_2-$ or $-CH_2$-phenylene-$CH_2-OCO-G_1-COO-CH_2$-phenylene-$CH_2-$ where $G_1$ is alkylene of 4 to 8 carbon atoms.

Preferably, when n is 3, T is 2,4,6-triazinyl or glyceryl.

When n is 4, T is preferably pentaerythrityl.

Preferably L and $L_o$ are the same and are $-CO$-phenylene-$CH_2-$ or $-CO-CH_2CH_2-$.

$R_7$ is preferably hydrogen, hydroxyl or alkyl of 4 to 8 carbon atoms. Most preferably $R_7$ is hydrogen, hydroxyl or butyl.

Preferred compounds of formula IV are those in which $L_3$ and $L_4$ are independently $-NR_5R_6$ or a group

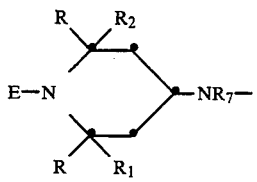

and $L_5$ is $-NR_5OH$.

It is contemplated that the alkyl and alkylene groups embrace both straight and branched chain moieties.

Alkyl is, for example, methyl, ethyl, isopropyl, n-butyl, isobutyl, tert-amyl, 2-ethylhexyl, lauryl, n-octadecyl or eicosyl.

Alkylene is, for example, methylene, ethylene, propylene, trimethylene, tetramethylene, neopentanediyl, hexamethylene, octamethylene or dodecamethylene.

Examples of other groups include the following:

alkenyl: allyl, but-2-enyl, oleyl;

cycloalkyl: cyclopentyl, cyclohexyl, cyclooctyl, cyclododecyl;

hydroxyalkyl: 2-hydroxyethyl, 2-hydroxypropyl, 3-hydroxypropyl;

alkanoyl: formyl, acetyl, propionyl, butyryl, valeroyl, caproyl, lauroyl, stearoyl;

alkoxy: methoxy, amyloxy, heptyloxy, octyloxy, nonyloxy, dodecyloxy;

aralkyl: benzyl, alpha-methylbenzyl, alpha,alpha-dimethylbenzyl;

arylene: o-phenylene, m-phenylene, p-phenylene, naphthylene;

xylylene: o-xylylene, m-xylylene, p-xylylene;

alkanetriyl: glyceryl, 1,2,4-butanetriyl, 1,2,6-hexanetriyl, 2-ethyl-isobutanetriyl;

alkanetetrayl: pentaerythrityl, 1,2,3,4-butanetetrayl;

alkyl interrupted by one or more oxygen atoms, preferably by one or two oxygen atoms: 3-oxapentanyl, 3-oxahexanyl, 3,6-dioxaoctanyl;

alkoxyalkyl: 2-methoxyethyl, 2-ethoxyethyl, 3-methoxypropyl, 3-ethoxypropyl, 3-butoxypropyl, 3-octoxypropyl, 4-methoxybutyl;

hydroxyaloxy: 2-hydroxyethoxy, 3-hydroxypropoxy;

alkoxyalkoxy: 2-methoxyethoxy, 2-ethoxyethoxy, 3-methoxypropoxy, 3-ethoxypropoxy, 3-butoxypropoxy, 3-octoxypropoxy;

cycloalkyloxy: cyclopentyloxy, cyclohexyloxy, cyclooctyloxy, cyclododecyloxy;

aryl: phenyl, naphthyl;

aryloxy: phenyloxy, naphthyloxy;

substituted aralkyl, in particular substituted phenylalkyl: methylbenzyl, dimethylbenzyl, t-butylbenzyl, chlorbenzyl;

aralkyloxy, preferably phenylalkyloxy: benzyloxy, alphamethylbenzyloxy, alpha,alpha-dimethylbenzyloxy;

bicycloaliphatic oxy radical or tricycloaliphatic oxy radical:

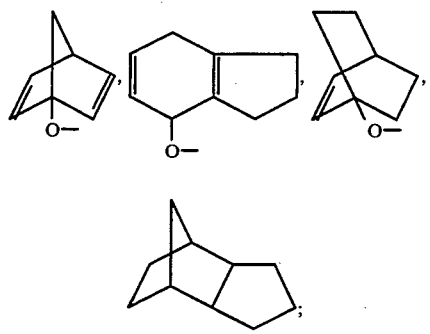

alkoxycarbonylalkyl: methoxycarbonylethyl, ethoxycarbonylethyl;

cycloalkylene: cyclohexylene;

arylene-alkylene, preferably phenylene-alkylene: phenylene-methylene;

alkyl substituted by dialkylamino: 2-dimethylaminoethyl, 2-diethylaminoethyl, 3-dimethylaminopropyl, 3-diethylaminopropyl, 3-dibutylaminopropyl, 4-diethylaminobutyl.

Where the term phenylene appears in structures of this invention, it relates to o-phenylene, m-phenylene or p-phenylene, preferably p-phenylene.

When $R_5$ and $R_6$, together with the nitrogen atom to which they are linked, form a 5-membered to 7-membered heterocyclic radical, representative examples are pyrrolidyl, piperidyl, morpholinyl, N-methylpiperazinyl and hexahydroazepinyl, preferably morpholinyl.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

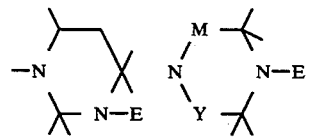

wherein M and Y are independently methylene or carbonyl, preferably M being methylene and Y being carbonyl. It is understood that the identified substituents applicable to such compounds are those which are appropriate for substitution on the ring nitrogen atoms.

The instant invention also pertains to stabilized compositions which comprise
  (a) a polymer subject to the deleterious effects of actinic light or of heat, and
  (b) an effective stabilizing amount of a compound of formula I, II, III or IV.

The instant compounds can be synthesized by a number of methods. These include N-alkylation of hydroxylamine or of a mono-substituted hydroxylamine; or by the hydrogenation of the corresponding nitrone.

Mono-substituted hydroxylamines already containing a hindered amine group can be prepared by hydrogenation of oxime derivatives of compounds containing hindered amine moieties. These same mono-substituted hydroxylamines can be condensed with aldehydes or ketones in order to prepare the corresponding nitrones.

Alternatively, the intermediate nitrones can be prepared by direct oxidation of secondary amines.

The starting materials needed to make the instant compounds are largely items of commerce or can be made by generally known methods.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone-acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes describe, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer such as Santolink XI 100 (Monsanto).
33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

In general, the compounds of formula I, II, III or IV can be added to polymeric materials before, during or after the polymerization or cross-linking of said materials.

The compounds of formula I, II, III or IV can be incorporated into the material to be stabilized in a pure form or encapsulated in waxes, oils or polymers.

The resulting stabilized polymer compositions of the invention may optionally also contain various conventional additives, such as the following.

1. Antioxidants
   1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
   1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
   1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
   1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
   1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate 1,3,5-tris-(3,5-di-tert-butyl-4-hydroxybenzyl)isocyanurate 1,3,5-tris-(4-tert-butyl-3-hydroxy-2,6-dimethylbenzyl)isocyanurate 3,5-di-tert-butyl-4-hydroxybenzyl-phosphoric acid dioctadecyl ester 3,5-di-tert-butyl-4-hydroxybenzyl-phosphoric acid monoethyl ester, calcium-salt 1.6. Acylaminophenols, for example, 4-hydroxy-lauric acid anilide 4-hydroxy-stearic acid anilide 2,4-bis-octylmercapto-6-(3,5-tert-butyl-4-hydroxyanilino)-s-triazine octyl-N-(3,5-di-tert-butyl-4-hydroxyphenyl)-carbamate 1.7. Esters of α-(3,5-di-tert-butyl-4-hydroxyphenyl)-propionic acid with monohydric or polyhydric alcohols, for example, methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid
diamide 1.8. Esters of β-(5-tert-butyl-4-hydroxy-3-methylphenyl)-propionic acid with monohydric or polyhydric alcohols, for example, methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid
diamide 1.9. Amides of α-(3,5-di-tert-butyl-4-hydroxyphenyl)-propionic acid for example, N,N'-di-(3,5-di-tert-butyl-4-hydroxyphenylpropionyl)-hexamethylenediamine N,N'-di-(3,5-di-tert-butyl-4-hydroxyphenylpropionyl)-trimethylenediamine N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, 3'-tert-butyl-5'-(2-octyloxycarbonyl)ethyl-, and dodecylated-5'-methyl derivatives.

2.2 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butyl-phenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyano-vinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert-butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert-butylphenyl)-phosphite, di-isodecylpentaerythritol diphosphite, di- (2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert-butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol 1 Part 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional storing lacquers described e.g. in H. Wagner and H. F. Sarx, op. cit., on pages 86–99.

The alkyd resin lacquers which can be stabilized against the action of light and moisture in accordance with the invention, are the conventional storing lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of the UV absorbers which may be used in the instant compositions in conjunction with the aforementioned piperidine compounds are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives (b) 2-Hydroxy-benzophenons, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-β,β-diphenylacrylic acid ethyl ester or isoctyl ester, alpha-carbomethoxy-cinnamic acid methyl ester, alpha-cyano-β-methyl-p-methoxy-cinnamic acid methyl ester or butyl ester, alphacarbomethoxy-p-methoxy-cinnamic acid methyl ester, N-(β-carbomethoxy-β-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octylox-yoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyl-oxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethyl-benzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresonding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

The compounds of formula I, II, III or IV can also be used as stabilizers, especially as light stabilizers, for almost all materials known in the art of photographic reproduction and other reproduction techniques as e.g. described in Research Disclosure 1990, 31429 (pages 474 to 480).

The following examples illustrate the embodiments of this invention. In these examples, any parts given are by weight unless otherwise specified.

EXAMPLE 1

N-Benzyl-N-(2,2,6,6-tetramethylpiperidin-4-yl)hydroxylamine

A mixture of 2,2,6,6-tetramethylpiperidin-4-one oxime (15.0 g, 88 mmol), 40 ml of 5N hydrochloric acid in methanol, 120 ml of methanol and 40 ml of water is subjected to 3 atmospheres of hydrogen over platinum oxide and 5% platinum on carbon for 18 hours. The reaction mixture is filtered through celite and concentrated. The crude hydroxylamine hydrochloride is added to 130 ml of N,N-dimethylformamide along with benzyl bromide (13.7 g, 80 mmol) and potassium carbonate (33.0 g, 240 mmol). The mixture is stirred for 16 hours. The mixture is then filtered and concentrated. The residue is partitioned between methylene chloride and dilute aqueous sodium carbonate. The organic layer is washed with water and brine, dried over anhydrous sodium sulfate and then concentrated to give 14.1 g of a white solid. This solid is recrystallized from ethanol to yield 6.8 g of the title compound in a 30% overall yield. The compound melts at 154° C.

$^1$H NMR (200 MHz, CDCl$_3$) δ7.30 (m, 5H's); 5.12 (s, 1 exchangeable H); 3.87 (s, 2H's); 3.12 (tt, 1H); 1.91 (dd, 2H's); 1.30–1.10 (m, 2H's); 1.15 (s, 6H's); 1.10 (s, 6H's). IR (CDCl$_3$) 3560, 3200 (broad), 3020, 2940, 1590 (weak) 1570 (weak), 1440, 1360, 1220, 1180, 1050, 1010, 1000 cm$^{-1}$. EIMS, m/z 262 (M$^+$) Analysis:

Calcd. for C$_{16}$H$_{26}$N$_2$O: C, 73.2; H, 10.0; N, 10.7. Found: C, 72.9; H, 10.1; N, 10.5.

EXAMPLE 2

N-Benzyl-N-(1,2,2,6,6-pentamethylpiperidin-4-yl)hydroxylamine

Following the procedure of Example 1, the title compound is prepared from 1,2,2,6,6-pentamethylpiperidin-4-one oxime (5.0 g, 27 mmol) and benzyl bromide (4.6 g, 27 mmol) in a 40% yield to give 3.0 g of a white solid which melts at 107°–108° C. after recrystallization from ethanol.

$^1$H NMR (200 MHz, CDCl$_3$) δ7.29 (brs, 5H's); 5.89 (one exchangeable H); 3.76 (s, 2H's); 2.97 (tt, 1H); 2.23 (s, 3H); 1.85 (dd, 2H's); 1.56 (t, 2H's); 1.15 (s, 6H's); 0.99 (s, 6H's). IR (CDCl$_3$) 3540, 3200 (broad), 3010, 2980, 1590, 1445, 1355, 1305, 1250, 1180, 1105, 1020 cm$^{-1}$. ELMS, m/z 276 (M$^+$) Analysis:

Calcd. for C$_{17}$H$_{28}$N$_2$O: C, 73.9; H, 10.2; N, 10.1. Found: C, 73.8; H, 10.2; N, 10.0.

EXAMPLE 3

N-Benzyl-N-(1-cyclohexyloxy-2,2,6,6-tetramethyl-piperidin-4-yl)-hydroxylamine

Following the procedure of Example 1, the title compound is prepared from 1-cyclohexyloxy-2,2,6,6-tetramethylpiperidin-4-one oxime (3.7 g, 13 mmol) and benzyl bromide (2.4 g, 14 mmol) in a 50% yield to give 2.3 g of product as white crystals melting at 133° C. after recrystalization from ethanol.

$^1$H NMR (200 MHz, CDCl$_3$) δ7.30 (m, 5H's); 3.72 (s, 2H's); 3.60 (m, 1H); 2.93 (tt, 1H); 2.24 (m, 2H's); 1.79 (m's, 4H's); 1.65 (t, 2H's); 1.22 (s, 6H's); 1.11 (s, 6H's); 1.6–1.0 (broad m, 6H's). IR (CDCl$_3$) 3570, 3200 (broad), 3020, 2920, 1595, 1440, 1350, 1240, 1180, 1170, 1050, 1040, 1010 cm$^{-1}$. EIMS, m/z 360 (M+) Analysis: Calcd. for C$_{22}$H$_{36}$N$_2$O$_2$: C, 73.3; H, 10.1; N, 7.8. Found: C, 73.7; H, 10.5; N, 7.6.

EXAMPLE 4

Lauryl 3-[N-(1-Octyloxy-2,2,6,6-tetramethylpiperidin-4-yl)-N-hydroxyamino]propionate A mixture of 1-octyloxy-2,2,6,6-tetramethylpiperidin-4-one oxime (10.0 g, 35.4 mmol) (a mixture of octyloxy isomers) 5.5 ml of concentrated hydrochloric acid and 130 ml of methanol is subjected to 3 atmospheres of hydrogen over 5% platinum on carbon for 18 hours. The reaction mixture is filtered through celite and then concentrated. The residue is partitioned between ethyl acetate and aqueous potassium carbonate. The organic layer is washed with water and brine, dried over anhydrous sodium sulfate and finally concentrated to a total volume of about 150 ml. Lauryl acrylate (7.7 g, 32 mmol) is added. After a two-hour reaction time, the reaction mixture is concentrated and the crude product purified by flash chromatography on silica gel (9:1, hexane:ethyl acetate) to yield 10.0 g (52% yield) of a clear oil.

$^1$H NMR (200 MHz, CDCl$_3$) δ5.63 (1 exchangeable H); 4.08 (t, 2H's); 3.95–3.54 (m, 1H); 3.00 (t, 2H's); 2.78 (tt, 1H); 2.63 (t, 2H's); 1.85–1.10 (m's, s at 1.30, s at 1.15, 48H's); 0.90 (m, 6H's). IR (CDCl$_3$) 3560, 3240 (broad), 2940, 1710, 1430, 1350, 1230, 1180, 1110, 1045, 1010 cm$^{-1}$. EIMS, m/z 540 (M+) Analysis: Calcd. for C$_{32}$H$_{64}$N$_2$O$_4$: C, 71.1; H, 11.9; N, 5.2. Found: C, 71.4; H, 12.5; N, 5.0.

EXAMPLE 5

Methyl 3-[N-(1-Octyloxy-2,2,6,6-tetramethylpiperidin-4-yl)-N-hydroxyamino]propionate When, following the general procedure of Example 4, an equivalent amount of methyl acrylate is substituted for lauryl acrylate, the title compound is prepared as a clear oil after flash chromatography on silica gel (3:1, hexane:ethyl acetate).

$^1$H NMR (200 MHz, CDCl$_3$) δ5.30 (1 exchangeable H); 3.69 (s, 3H's); 3.90–3.64 (m, 1H); 3.02 (t, 2H's); 2.87 (tt, 1H); 2.63 (t, 2H's); 1.73 (m, 2H's); 1.52 (t, 2H's); 1.50–0.80 (complex m's, 28H's). IR (CDCl$_3$) 3560, 3200 (broad), 2940, 1715, 1430, 1350, 1190, 1170, 1055, 1015 cm$^{-1}$. EIMS, m/z 386 (M+) Analysis:

Calcd. for C$_{21}$H$_{42}$N$_2$O$_4$: C, 65.2; H, 10.9; N, 7.2. Found: C, 65.0; H, 10.7; N, 7.2.

EXAMPLE 6

Hexamethylene Di-3-[N-(1-octyloxy-2,2,6,6-tetramethylpiperidin-4-yl)-N-hydroxyamino]propionate The title compound is prepared from 1-octyloxy-2,2,6,6-tetramethylpiperidin-4-one oxime (9.4 g, 31.4 mmol) (a mixture of octyloxy isomers) and hexamethylene diacrylate (3.2 g, 14.0 mmol) following the procedure of Example 4 in a 56% yield (7.3 g) as a thick oil after flash chromatography on silica gel (4:1, hexane:ethyl acetate).

$^1$H NMR (200 MHz, CDCl$_3$) δ6.39 (2 exchangeable H's); 4.11 (t, 4H's); 3.9–3.6 (m's, 2H's); 3.20 (t, 4H's); 2.91 (tt, 2H's); 2.64 (t, 4H's); 1.7–0.9 (all remaining H's). IR (CDCl$_3$) 3560, 3200 (broad), 2900, 1710, 1430, 1350, 1230, 1170, 1110, 1045, 1000 cm$^{-1}$. CIMS (CH$_4$), m/z 827 (M++H) Analysis: Calcd. for C$_{46}$H$_{90}$N$_4$O$_8$: C, 66.8; H, 11.0; N, 6.8. Found: C, 67.2; H, 11.2; N, 6.7.

EXAMPLE 7

N-(1-Acetyl-2,2,6,6-tetramethylpiperidin-4-yl)-N-butylhydroxylamine

A solution of N-(1-acetyl-2,2,6,6-tetramethylpiperidin-4-yl)-alpha-nitrone (4.8 g, 17.8 mmol) and 40 ml of methanol is subjected to 3 atmospheres of hydrogen over 5% platinum on carbon for one hour. The reaction mixture is then filtered through celite and concentrated. The crude hydroxylamine is purified by flash chromatography on silica gel (9:1, hexane:ethyl acetate) to yield 3.5 g (73% yield) of the title compound as a white solid melting at 52°–54° C.

$^1$H NMR (200 MHz, CDCl$_3$) δ5.2 (1 exchangeable H); 2.95 (quint, 1H); 2.63 (t, 2H's); 2.18 (s, 3H's); 1.93 (d, 4H's); 1.7–1.2 (m, 4H's); 1.53 (s, 6H's); 1.45 (s, 6H's); 0.93 (t, 3H's). IR (CDCl$_3$) 3570, 3200 (broad), 2940, 1600, 1430, 1359, 1330, 1270, 1165, 1005 cm$^{-1}$. EIMS, m/z 270 (M+) Analysis: Calcd. for C$_{15}$H$_{30}$N$_2$O$_2$: C, 66.6; H, 11.2; N, 10.4.

Found: C, 66.7; H, 11.2; N, 10.3.

EXAMPLE 8

N-Isobutyl-N-(1-octyloxy-2,2,6,6-tetramethylpiperidin-4-yl)-hydroxylamine

Following the procedure Example 7, the title compound is prepared from alpha-isopropyl-N-(1-octyloxy-2,2,6,6-tetramethylpiperidin-4-yl)nitrone (2.0 g, 5.6 mmol) (a mixture of octyloxy isomers) in an 80% yield (1.6 g) as a clear oil after flash chromatography on silica gel (9:1, hexane:ethyl acetate).

$^1$H NMR (200 MHz, CDCl$_3$) δ5.75 (1 exchangeable H); 3.70 (m's, 1H); 2.90 (tt, 1H); 2.50 (d, 2H); 1.7 (m, 5H's); 1.45–0.80 (all remaining H's). IR (neat) 3300, 2920, 1480, 1360, 1250, 1180, 1160, 1110, 1065, 950 cm$^{-1}$. EIMS, m/z 356 (M+) Analysis: Calcd. for C$_{21}$H$_{44}$N$_2$O$_2$: C, 70.7; H, 12.4; N, 7.9. Found: C, 71.2; H, 12.7; N, 7.6.

EXAMPLE 9

N,N'-Dihydroxy-N,N'-bis-(1-octyloxy-2,2,6,6-tetramethylpiperidin-4-yl)-hexamethylenediamine Following the procedure of Example 7, the title compound is prepared from 1,8-bis-(1-octyloxy-2,2,6,6-tetramethylpiperidin-4-yl)-1,8-diazaocta-1,7-diene N,N'-bisoxide (2.7 g, 4.0 mmol) (a mixture of octyloxy isomers) in 47% yield (1.3 g) as a heavy oil after flash chromatography on silica gel (9:1, ethyl acetate:methanol).

$^1$H NMR (200 MHz, CDCl$_3$) δ7.09 (2 exchangeable H's); 3.9–3.6 (m's, 2H's); 2.91 (m, 2H's); 2.68 (t, 4H's); 1.9–0.8 (m's, all remaining H's). IR (neat) 3240, 2940, 1450, 1370, 1240, 1180, 1170, 1120, 1080, 960 cm$^{-1}$. CIMS (CH$_4$), m/z 683 (M++H) Analysis: Calcd. for C$_{40}$H$_{82}$N$_4$O$_4$: C, 70.3; H, 12.1; N, 8.2.

Found: C, 70.5; H, 12.4; N, 8.1.

EXAMPLE 10

N,N-Bis-[4-(1-cyclohexyloxy-2,2,6,6-tetramethylpiperidin-4-yloxycarbonyl)benzyl]hydroxylamine To a solution of 1-cyclohexyloxy-2,2,6,6-tetramethylpiperidin-4-yl 4-chloromethylbenzoate (4.8 g, 11.8 mmol) in 35 ml of N,N-dimethylformamide at 55° C. is added sodium carbonate (3.4 g, 32.4 mmol) and hydroxylamine hydrochloride (470 mg, 6.8 mmol). The mixture is stirred at 55°-65° C. for 20 hours and then concentrated. The residue is partitioned between methylene chloride and water. The organic layer is washed with water and brine, dried over anhydrous sodium sulfate and finally concentrated to leave 6 g of a heavy oil which is purified by flash chromatography on silica gel (7:1, heptane:ethyl acetate). The product is then recrystallized from ethanol to give 2.3 g (50% yield) of the title compound as a white solid melting at 163°-166° C.

$^1$H NMR (200 MHz, CDCl$_3$) $\delta$7.98 (d, 4H's); 7.45 (d, 4H's); 5.26 (tt, 2H's); 5.19 (1 exchangeable H); 3.92 (s, 4H's); 3.64 (m, 2H's); 2.06 (m, 4H's); 1.96 (m, 4H's); 1.8-1.0 (m's, all remaining H's). IR (CDCl$_3$) 3550, 2900, 2915, 1690, 1600, 1570, 1430, 1400, 1350, 1300, 1260, 1230, 1160, 1100, 1045, 1030, 1010, 990 cm$^{-1}$. EIMS of the trimethylsilyl derivative, m/z 847 (M+) Analysis: Calcd. for C$_{46}$H$_{69}$N$_3$O$_7$: C, 71.2; H, 9.0; N, 5.4. Found: C, 71.0; H, 9.1; N, 5.3.

Following the general procedure of Example 1, the following compounds are prepared by reaction of the appropriate equivalent amounts of the indicated starting materials.

EXAMPLE 11

N,N'-Dihydroxy-N,N'-bis-(2,2,6,6-tetramethylpiperidin-4-yl)-hexamethylenediamine from 2,2,6,6-tetramethylpiperidin-4-one oxime and 1,6-dibromohexane

EXAMPLE 12

N,N'-Dihydroxy-N,N'-bis-(2,2,6,6-tetramethylpiperidin-4-yl)-p-xylylenediamine from 2,2,6,6-tetramethylpiperidin-4-one oxime and p-xylene dibromide

EXAMPLE 13

Hexamethylene Di-[4-(N-(2,2,6,6-tetramethylpiperidin-4-yl)-N-hydroxyaminomethyl)benzoate]

from 2,2,6,6-tetramethylpiperidin-4-one oxime and hexamethylene di-(4-bromomethylbenzoate)

EXAMPLE 14

Di-[4-(N-(2,2,6,6-tetramethylpiperidin-4-yl)-N-hydroxyaminomethyl)benzyl]sebacate from 2,2,6,6-tetramethylpiperidin-4-one oxime and di-(4-bromomethylbenzyl)sebacate Following the general procedure of Example 10, the following compounds are prepared from the appropriate equivalent amounts of the indicated starting materials.

EXAMPLE 15

N,N-Bis-[4-(2,2,6,6-tetramethylpiperidin-4-yloxycarbonyl)benzyl]hydroxylamine from 2,2,6,6-tetramethylpiperidin-4-yl 4-chloromethylbenzoate and hydroxylamine

EXAMPLE 16

N,N-Bis-[4-(N,N-bis-(2,2,6,6-tetramethylpiperidin-4-yl)amino)-carbonylbenzyl]hydroxylamine from N,N-bis(2,2,6,6-tetramethylpiperidin-4-yl)-4-chloromethylbenzamide and hydroxylamine

EXAMPLE 17

N,N-Bis-[2-(N,N-bis-(2,2,6,6-tetramethylpiperidin-4-yl)amino)-carbonylethyl]hydroxylamine from N,N-bis-(2,2,6,6-tetramethylpiperidin-4-yl)acrylamide and hydroxylamine The following compounds are prepared by the reaction of 2,4,6-trichloro-s-triazine (cyanuric chloride) with the appropriate equivalent amounts of hydroxylamine and the third starting material listed below.

EXAMPLE 18

2-Hydroxyamino-4,6-bis-[(2,2,6,6-tetramethylpiperidin-4-yl)amino]-s-triazine from 2,2,6,6-tetramethylpiperidin-4-ylamine

EXAMPLE 19

2-Hydroxyamino-4,6-bis-[(2,2,6,6-tetramethylpiperidin-4-yl)hydroxyamino]-s-triazine from N-(2,2,6,6-tetramethylpiperidin-4-yl)hydroxylamine

EXAMPLE 20

2-Hydroxyamino-4,6-bis[N-(2,2,6,6-tetramethyl-4-piperidyl)n-butylamino]-1,3,5-triazine from N-(2,2,6,6-tetramethyl-4-piperidyl)-n-butylamine m.p. 235°-237° C.

EXAMPLE 21

2-Hydroxyamino-4,6-bis[N-(2,2,6,6-tetramethyl-4-piperidyl)-2,2,6,6-tetramethyl-4-piperidylamino]-1,3,5-triazine from N-(2,2,6,6-tetramethyl-4-piperidyl)-2,2,6,6-tetramethyl-4-piperidylamine m.p. 178°-182° C.

EXAMPLE 22

2-Hydroxyamino-4,6-bis[N-(2,2,6,6-tetramethyl-4-piperidyl)-n-dodecylamino]-1,3,5-triazine from N-(2,2,6,6-tetramethyl-4-piperidyl)-n-dodecylamine m.p. 44°-45° C.

EXAMPLE 23

2-Hydroxyamino-4-morpholinyl-6-[N-(2,2,6,6-tetramethyl-4-piperidyl)-2,2,6,6-tetramethyl-4-piperidylamino]-1,3,5-triazine from N-(2,2,6,6-tetramethyl-4-piperidyl)-2,2,6,6-tetramethyl-4-piperidylamine and morpholine m.p. 250°-254° C.

The following compounds are prepared by the reaction of 2-chloro-4,6-bis(1,2,2,6,6-pentamethyl-4-piperidyl)-1,3,5-triazine derivatives with the appropriate equivalent amounts of hydroxylamine.

The suitable 2-chloro-4,6-bis(1,2,2,6,6-pentamethyl-4-piperidine)-1,3,5-triazine derivatives are listed below.

EXAMPLE 24

2-Hydroxyamino-4,6-bis[N-(1,2,2,6,6-pentamethyl-4-piperidyl)-n-butylamino]-1,3,5-triazine from 2-chloro-4,6-bis[N-(1,2,2,6,6-pentamethyl-4-piperidyl)-n-butylamino]-1,3,5-triazine m.p. 104°–107° C.

EXAMPLE 25

2-Hydroxyamino-4,6-bis[N-(1,2,2,6,6-pentamethyl-4-piperidyl)-1,2,2,6,6-pentamethyl-4-piperidylamino]-1,3,5-triazine from 2-chloro-4,6-bis[N-(1,2,2,6,6-pentamethyl-4-piperidyl)-1,2,2,6,6-pentamethyl-4-piperidylamino]-1,3,5-triazine m.p. 293°–298° C.

EXAMPLE 26

2-Hydroxyamino-4,6-bis[N-(1,2,2,6,6,-pentamethyl-4-piperidyl)tetrahydrofurfurylamino]-1,3,5-triazine from 2-chloro-4,6-bis[N-(1,2,2,6,6-pentamethyl-4-piperidyl)tetrahydrofurfurylamino]-1,3,5-triazine m.p. 110°–114° C.

EXAMPLE 27

2-Hydroxyamino-4-morpholinyl-6-[N-(1,2,2,6,6-pentamethyl-4-piperidyl)-1,2,2,6,6-pentamethyl-4-piperidylamino]-1,3,5-triazine from 2-chloro-4-morpholinyl-6-[N-(1,2,2,6,6-pentamethyl-4-piperidyl)-1,2,2,6,6-pentamethyl-4-piperidylamino]-1,3,5-triazine m.p. 237°–241° C.

EXAMPLE 28

2-Hydroxyamino-4,6-bis[N-(1,2,2,6,6-pentamethyl-4-piperidyl)methylamino]-1,3,5-triazine from 2-chloro-4,6-bis[N-(1,2,2,6,6-pentamethyl-4-piperidyl)methylamino]-1,3,5-triazine, m.p. 157°–160° C.

EXAMPLE 29

2-N-Methylhydroxyamino-4,6-bis[N-(1,2,2,6,6-pentamethyl-4-piperidyl)-n-butylamino]-1,3,5-triazine from 2-chloro-4,6-bis[N-(1,2,2,6,6-pentamethyl-4-piperidyl)-n-butylamino]-1,3,5-triazine and N-methylhydroxyamine, m.p. 108°–110° C.

EXAMPLE 30

Light Stabilization of Polypropylene

This example illustrates the light stabilizing effectiveness of instant stabilizers.

Polypropylene (®Himont Profax 6501) powder stabilized with 0.2% by weight of n-octadecyl 3,5-tert-butyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi (1.2 × 10⁶ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
| --- | --- | --- |
| Control* | — | 340 |
| Example 1 | 0.1 | 820 |
| Example 3 | 0.1 | 1150 |
| Example 8 | 0.1 | 1040 |
| Example 10 | 0.1 | 1060 |

*Base resin plus 0.1% calcium stearate and 0.2 of n-octadecyl 3,5-di-tert-butyl-4-hydroxyhydrocinnamate.

EXAMPLE 31

Process Stabilization of Polypropylene at 536° F. (280° C.)

The base formulation comprises 100 parts of polypropylene (®Profax 6501, Himont) with 0.10 parts of calcium stearate and 0.10 parts of neopentanetetrayl tetrakis (3,5-di-tert-butyl-4-hydroxyhydrocinnamate). The test stabilizer is solvent blended onto the propylene from a solution in methylene chloride. After removal of the solvent by evaporation under reduced pressure, the stabilized resin formulation is extruded at 100 rpm from a 1 inch (2.54 cm) diameter extruder at 500° F. (260° C.).

After each of the first and fifth extrusions, resin pellets are compression molded into 125 mil (3.2 mm) thick plaques at 380° F. (193° C.) and specimen yellowness index (YI) is determined according to ASTM D-1925. Low YI values indicate less yellowing. Additionally, the melt flow rate (in grams/10 minutes) according to ASTM D-1238 is measured on the pellets after the first and fifth extrusions. The closer the melt flow rate after the fifth extrusion is to the melt flow rate after the first extrusion indicates superior process stabilization of the polypropylene.

| Additive Compound of * | Stab. Conc. % by wt. | Yellowness Index Color After Extrusion | | Melt Flow Rate After Extrusion | |
| --- | --- | --- | --- | --- | --- |
| | | 1 | 5 | 1 | 5 |
| Base (first) Formulation | — | 9.1 | 17.7 | 12.6 | 22.8 |
| Example 1 | 0.05 | 8.2 | 14.4 | 5.8 | 12.7 |
| Base (second) | — | 8.4 | 10.5 | 4.3 | 12.7 |
| Example 2 | 0.05 | 2.9 | 9.7 | 2.6 | 10.1 |

*Base formulation contains 0.1% of calcium stearate plus 0.1% of neopentinetetrayl tetrakis (3,5-di-tert-butyl-4-hydroxyhydrocinnamate)

The instant stabilizer plus phenolic antioxidant exhibits better process stabilization protection to the polypropylene in both resistance to discoloration and in resistance to polymer degradation than does the phenolic antioxidant alone.

EXAMPLE 32

Process Stabilization of Polypropylene at 536° F. (280° C.)

Following the general procedure of Example 31, the process stabilization of old technology polypropylene (®Profax 6501, Himont) containing only 0.1% by weight of calcium stearate is determined at 536° F. (280° C.) in the presence of a test additive. The results of yellowness (YI index) and melt flow rate, (g/10 minutes) values are seen in the table below.

| Additive Compound of * | Stab. Conc. % by wt. | Yellowness Index Color After Extrusion | | Melt Flow Rate After Extrusion | |
|---|---|---|---|---|---|
| | | 1 | 5 | 1 | 5 |
| AO I | 0.1 | 7.8 | 13.5 | 5.4 | 11.4 |
| Example 1 | 0.05 | 3.5 | 5.8 | 2.7 | 5.6 |
| Example 2 | 0.05 | 2.7 | 8.9 | 3.0 | 10.6 |

*Base resin contains only 0.1% by weight of calcium stearate

AO I is neopentanetetrayl tetrakis-(3,5-di-tert-butyl-4-hydroxyhydrocinnamate)

The instant stabilizers are more effective than the phenolic antioxidant in providing the polypropylene protection from discoloration or polymer degradation.

EXAMPLE 33

Process Stabilization of Polypropylene at 536° F. (280° C.)

The base formulation comprises unstabilized, new technology polypropylene (®Profax 6501, Himont) with 0.1% by weight of calcium stearate present. The test stabilizer is solvent blended onto the polypropylene from a solution in methylene chloride. After removal of the solvent by evaporation under reduced pressure, the stabilized resin formulation is extruded at 100 rpm from a 1 inch (2.54 cm) diameter extruder at 536° F. (280° C.).

After each of the first and fifth extrusions, resin pellets are compression molded into 125 mil (3.2 mm) thick plaques at 380° F. (193° C.) and specimen yellowness index (YI) is determined according to ASTM D-1925. Low YI values indicate less yellowing. Additionally, the melt flow rate (in grams/10 minutes) according to ASTM D-1238 is measured on the pellets after the first and fifth extrusions. The closer the melt flow rate after the fifth extrusion is to the melt flow rate after the first extrusion the less polymer degradation has occurred. This would indicate superior process stabilization efficacy of the test stabilizer.

The instant compounds provide good process stabilization to polypropylene as seen by melt flow rate values.

EXAMPLE 34

Stabilization of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4"×12" (10.16 cm×30.48 cm) panels (®Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

What is claimed is:

1. A compound of formula IV

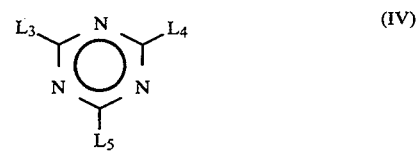

(IV)

wherein

E is hydrogen, oxyl, hydroxyl, alkyl of 1 to 18 carbon atoms, alkenyl of 3 to 18 carbon atoms, aralkyl of 7 to 9 carbon atoms, cycloalkyl of 5 to 12 carbon atoms, hydroxyalkyl of 2 to 6 carbon atoms, alkoxyalkyl of 2 to 20 carbon atoms, alkanoyl of 1 to 18 carbon atoms, alkoxy of 1 to 18 carbon atoms, cycloalkoxy of 5 to 12 carbon atoms, aryloxy of 6 to 10 carbon atoms, hydroxyalkoxy of 2 to 6 carbon atoms, alkoxyalkoxy of 2 to 20 carbon atoms, aralkoxy of 7 to 15 carbon atoms or a bicyclo or tricycloaliphatic oxy radical of 7 to 12 carbon atoms, R and $R_1$ are independently alkyl of 1 to 4 carbon atoms or together R and $R_1$ are pentamethylene, $L_3$, $L_4$ and $L_5$ are independently —$NR_5OH$, —$OR_4$, —$SR_4$ or —$NR_5R_6$ where $R_4$ is alkyl of 1 to 18 carbon atoms, and $R_5$ and $R_6$ are independently hydrogen, alkyl of 1 to 18 carbon atoms, 2,2,6,6-tetramethyl-4-piperidyl, 1,2,2,6,6-pentamethyl-4-piperidyl, tetrahydrofurfuryl, $C_2$–$C_4$-alkyl which is substituted in the 2-, 3- or 4-position by OH, by $C_1$–$C_8$-alkoxy or by di($C_1$–$C_4$-alkyl)amino, or —$NR_5R_6$ is pyrrolidyl, piperidyl, morpholinyl, N-methylpiperazinyl or hexahydroazepinyl, or $L_3$, $L_4$ and $L_5$ are independently

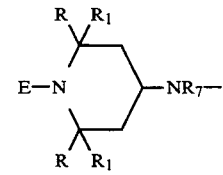

where $R_7$ is hydrogen, hydroxyl, alkyl of 1 to 12 carbon atoms or

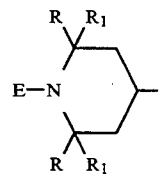

with the provisio that at least one of $L_3$, $L_4$ and $L_5$ is

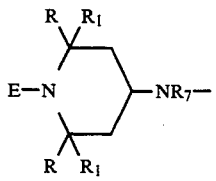

where R₇ is hydroxyl, or is —NR₅OH.

2. A compound according to claim 1 wherein R and R₁ are each methyl.

3. A compound according to claim 1 wherein E is hydrogen, hydroxyl, alkyl of 1 to 12 carbon atoms, allyl, benzyl, alkanoyl of 2 to 4 carbon atoms, alkoxy of 1 to 12 carbon atoms, cyclohexyloxy or alpha-methylbenzyloxy.

4. A compound according to claim 3 wherein E is hydrogen, hydroxyl, alkyl of 1 to 4 carbon atoms, allyl, benzyl, acetyl, methoxy, heptyloxy, octyloxy, nonyloxy or cyclohexyloxy.

5. A compound according to claim 1 wherein R₇ is hydrogen, hydroxyl or alkyl of 4 to 8 carbon atoms.

6. A compound according to claim 5 wherein R7 is hydrogen, hydroxyl or butyl.

7. The compound according to claim 1 which is 2-hydroxyamino-4,6-bis[N-(2,2,6,6-tetramethyl-4-piperidyl)-n-butylamino]-1,3,5-triazine;
2-hydroxyamino-4,6-bis[N-(2,2,6,6-tetramethyl-4-piperidyl)-2,2,6,6-tetramethyl-4-piperidylamino]-1,3,5-triazine;
2-hydroxyamino-4,6-bis[N-(2,2,6,6-tetramethyl-4-piperidyl)-n-dodecylamino]-1,3,5-triazine;
2-hydroxyamino-4-morpholinyl-6-[N-(2,2,6,6-tetramethyl-4-piperidyl)-2,2,6,6-tetramethyl-4-piperidylamino]-1,3,5-triazine;
2-hydroxyamino-4,6-bis[N-(1,2,2,6,6-pentamethyl-4-piperidyl)-n-butylamino]-1,3,5-triazine;
2-hydroxyamino-4,6-bis[N-(1,2,2,6,6-pentamethyl-4-piperidyl)-1,2,2,6,6-pentamethyl-4-piperidylamino]-1,3,5-triazine;
2-hydroxyamino-4,6-bis[N-(1,2,2,6,6-pentamethyl-4-piperidyl)tetrahydrofurfurylamino]-1,3,5-triazine;
2-hydroxyamino-4-morpholinyl-6-[N-(1,2,2,6,6-pentamethyl-4-piperidyl)-1,2,2,6,6-pentamethyl-4-piperidylamino]-1,3,5-triazine;
2-hydroxyamino-4,6-bis[N-(1,2,2,6,6-pentamethyl-4-piperidyl)methylamino]-1,3,5-triazine; or
2-N-methylhydroxyamino-4,6-bis[N-(1,2,2,6,6-pentamethyl-4-piperidyl)-n-butylamino]-1,3,5-triazine.

* * * * *